United States Patent [19]

Dolan

[11] Patent Number: 4,732,321
[45] Date of Patent: Mar. 22, 1988

[54] PASSIVE AIR FRESHENER

[76] Inventor: John E. Dolan, 15 New Main St., Haverstraw, N.Y. 10927

[21] Appl. No.: 886,415

[22] Filed: Jul. 17, 1986

[51] Int. Cl.$^4$ ............................................. A61L 9/04
[52] U.S. Cl. ...................................... 239/45; 239/47; 239/51.5
[58] Field of Search ...................... 239/44, 45, 47, 50, 239/515, 53–56; 222/187

[56] References Cited

U.S. PATENT DOCUMENTS

| 3,400,890 | 9/1968 | Gould | 239/54 X |
| 3,587,968 | 6/1971 | Hennart | 239/309 X |
| 4,165,835 | 8/1979 | Dearling | 230/45 X |
| 4,621,768 | 11/1986 | Lhoste et al. | 239/51.5 |

Primary Examiner—Andres Kashnikow
Assistant Examiner—Kevin P. Weldon
Attorney, Agent, or Firm—John F. Ohlandt

[57] ABSTRACT

A room deodorizer that relies on the fact that oil and water do not mix and that oil is lighter than water, to the end that water can be used to drive the perfume oils out of a paper matrix or the like by molecular displacement consequently, instead of having a perfume solution moving up a wick, it is provided that water rises from a reservoir by capillary action into an upper portion of a wick which is impregnated with perfume oil, and because of the molecular displacement of the oil by the water, the perfume oil is thereby driven to the surface when it evaporates into the ambient.

9 Claims, 10 Drawing Figures

U.S. Patent  Mar. 22, 1988  Sheet 1 of 3  4,732,321
FIG.1
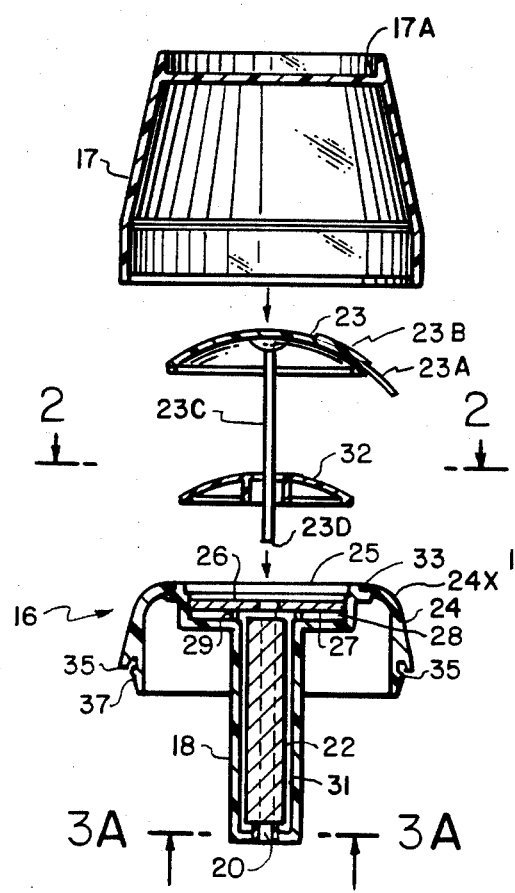
FIG.2
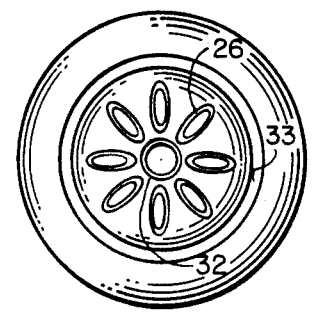
FIG.2A
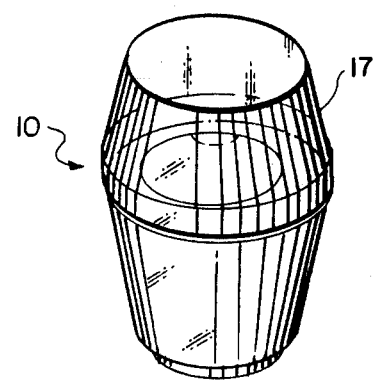
FIG.3A
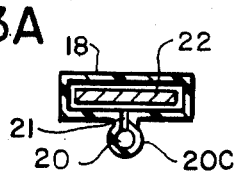
FIG.3

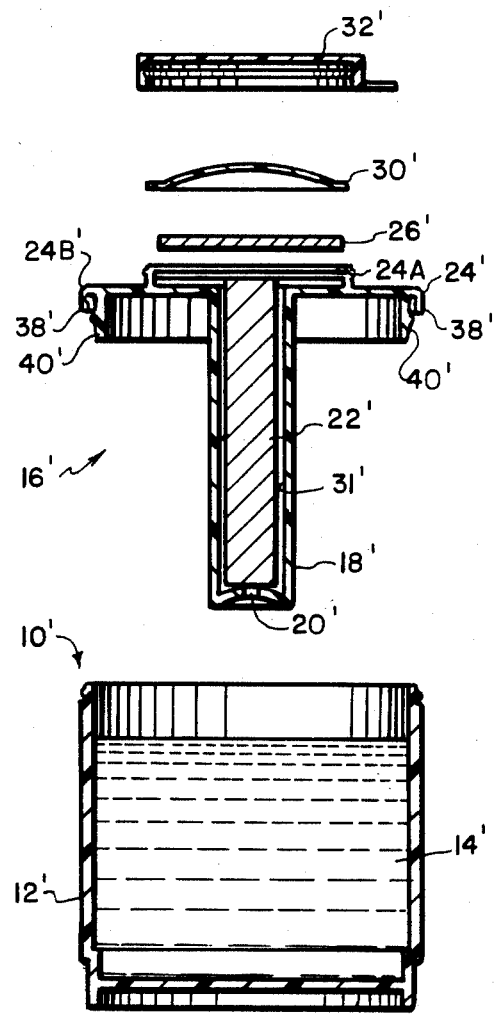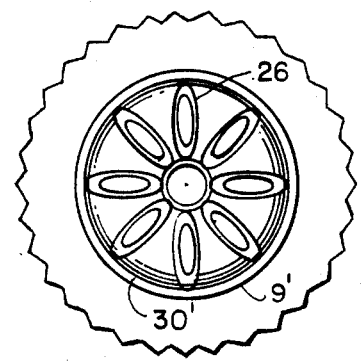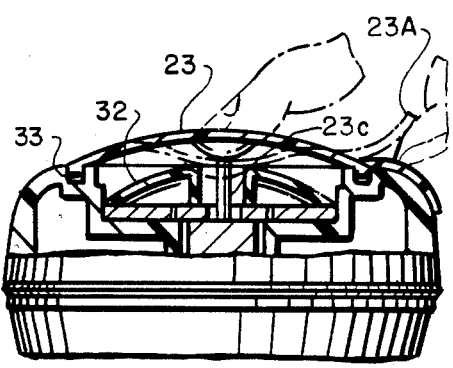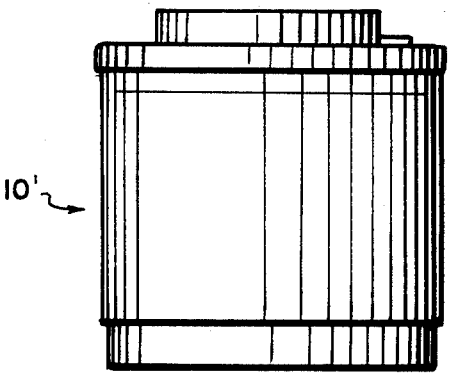

PASSIVE AIR FRESHENER

BACKGROUND OF THE INVENTION

The present invention relates to a room deodorizer or air freshener and, more particularly, to the type that dispenses perfume into the air by relying on movement of a liquid or solution up a wick such that exposure of the wick to the air allows the liquid to evaporate.

A variety of room deodorizers of the type described above have been known in the art, but basically these provide that a solution consisting of perfume oil, emulsifiers, alcohol and water, is permitted to move up a wick by capillary action. The problem with this approach is that the wick or paper matrix also acts like a filter and hence the perfume is not evenly dispensed. As a consequence, there is a limitation imposed of using only those fragrances that minimize this problem. However, the objective of a room deodorizer is generally to be able to use the fragrance that will do the best job, so that one will not be limited to the type of perfume that will be moved up the wick with the least resistance.

Accordingly, it is a primary object of the present invention to provide an economical and effective room deodorizer that will freshen a room evenly over a 30 to 60 day period, the time period depending on the amount of liquid in the lower portion of the dispenser.

Another primary object is to insure that the perfume is uniformly dispensed throughout the time period involved.

The above and other objects are implemented by several features of the present invention. In accordance with the primary feature, the room deodorizer enables continuously dispensing a deodorant over an extended period of time by having a matrix, preferably made of paper, disposed within a container which holds a quantity of a first liquid that is not miscible with a second liquid. The matrix has a first portion partly immersed in the first liquid, which is usually water, and is provided with a second portion impregnated with a second liquid in the form of perfume oil. These two portions can actually be constituted—and are indeed so constituted in the preferred embodiments—of respective, separate first and second matrix elements. The key aspect is that water within the container moves upward in the matrix by capillary action and contacts the perfume oil in the second portion of the matrix, whereby the perfume oil is forced to the surface by molecular displacement since the water and oil will not mix. Hence, the perfume oil evaporates into the atmosphere. Such evaporation will take place over a long period of the order of 60 days such that a uniform dispensing takes place over that period.

Other and further objects, advantages and features of the present invention will be understood by reference to the following specification in conjunction with the annexed drawing, wherein like parts have been given like numbers.

BRIEF DESCRIPTION OF DRAWING

FIG. 1 is an exploded view, partly in section, of the room deodorizer device in accordance with the first preferred embodiment of the invention;

FIG. 2 is a top plan view of the device taken on the line 2—2 of FIG. 1, the outer cover having been removed from the device;

FIG. 2A is a fragmentary view of the top of the room deodorizer device in the situation where the device has been activated;

FIG. 2B is another fragmentary view which illustrates the operation by the consumer in removing the device cap which causes device actuation;

FIG. 3 is an elevation view showing all of the parts of the deodorizer previously illustrated in FIG. 1, herewith completely assembled for use;

FIG. 3A is a view looking from the bottom of the cover assembly;

FIG. 4 is an exploded view, partly in section, of an alternate preferred embodiment of the invention;

FIG. 5 is a top plan view of the device, taken on the line 5—5 of FIG. 4;

FIG. 6 is an elevation view showing all of the parts of the deodorizer previously illustrated in FIG. 4, herewith completely assembled for use.

DESCRIPTION OF PREFERRED EMBODIMENTS

Figure 1A:
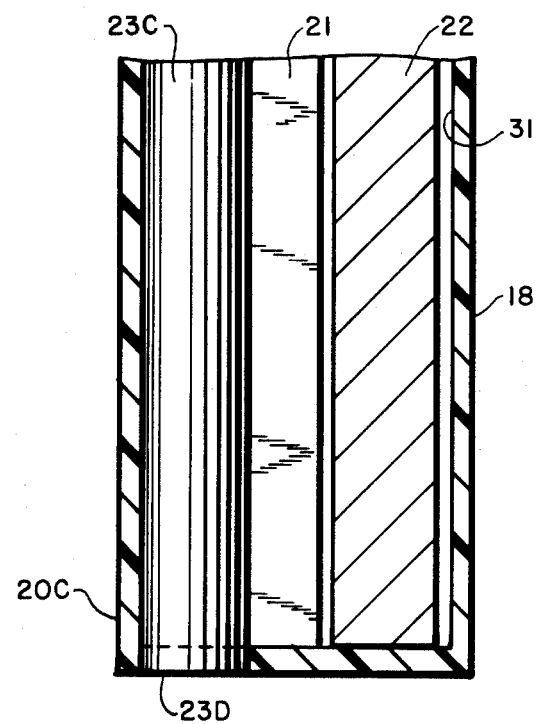
FIG. 1A is a fragmentary vertical sectional view, particularly illustrating blocking of the opening 20 in the cover member when it is desired that water not reach the matrix 22 unless cap 23 has been removed.

Referring now to the figures of the drawing, and initially to FIGS. 1-3, there will be seen the preferred embodiment of a room deodorizer device 10 comprising a container 12 for holding a liquid 14, preferably water, within the container.

Fitted to the top of container 12 is an inner cover assembly 16, which typically is constituted of plastic such as polypropylene. An outer transparent cover 17 is employed for the purpose of shipping, labeling and stacking; the consumer removes this outer cover when ready to use the product, such cover 17 typically having a recess 17A and being constituted of styrene.

The cover assembly 16 is formed to include a downwardly extending tube 18 adjacent which a hollow sleeve 20C extends, the sleeve being provided with an opening 20 at its bottom portion (FIG. 3A). Within the tube 18, an elongate mtrix element 22 is retained, this matrix element preferably being made of paper. The whole cover assembly 16, including the tube 18, may be fabricated as an integral or unitary entity. Alternately, the tube 18 can be made separately from the rest of the assembly, and subsequently affixed thereto. At the top of the tube 18 there is formed a dome-shaped cover member 24. This member 24 is adapted to receive or accommodate a second matrix element 26 in the form of a disk made of paper, recess 25 being provided for this purpose. A cap 23 fits into a groove 33 spaced from recess 25 at the top of member 24. The cap includes a tab 23A which is manipulatable by the consumer; and is shaped to abut against the curved upper surface 24X of member 24. Also included is a rib 23B on the cap so as to insure that the consumer will have to press down on the center of the cap to permit lifting of the tab, thereby to enable removal of the cap. The cap is further provided with a rod 23C adapted to extend into sleeve 20C and to block, by means of tip 23D, opening 20, so that water cannot reach matrix 22 under any circumstances unless cap 23 has been removed. When the rod 23C is lifted from the opening 20, water can then reach matrix 22 by way of the slotted passageway 21 in tube 18 (FIG. 3A).

The disk 26 has a bottom 27 which normally is so spaced, by reason of the presence of spikes 29, from the top of the first matrix element 22 that a gap 28 is defined. This gap normally insures that, prior to use by the consumer, i.e. when the deodorizer device is first assembled, there will not be contact between the first and second matrix elements so that, even though the first matrix element 22 is immersed in the water present in container 12, water will not move up into the disk or second matrix element 26.

When the cap 23 is removed by the consumer so as to expose the disk matrix 26 there is a grill 32 disposed above the disk to protect the disk 26. As just noted, the consumer has to press down on the center of the cap 23 to place the product in use, such pressure coincidently producing the desired result of having the grill 32 force disk 26 downwardly against spikes 29, thereby placing disk 26 in contact with the top of the wick or first matrix element 22. Consequently, the capillary action causes the water which has risen in the wick 22 to contact the disk 26 and to rise within it.

In assembling the room deodorizer 10, the various elements depicted in FIG. 1 are brought together as seen in FIG. 3. The cap 23 is snapped into place in the aforenoted groove 33. The whole top, i.e., cover assembly 16, is snapped into engagement with grooves 34 at the rim of container 12 by reason of the presence of ridges 35 and 37 on member 24. This action establishes an air-tight seal for the deodorizer. Prior to this, however, the disk 26 (having a diameter in the typical version of 1 9/16 inches) is impregnated with 3 grams of perfume and oil extenders such as mineral oil, propylene glycol, etc.

As noted previously, the perfume oil thus placed in the disk 26 is pushed to the upper surface thereof by the water 14 which rises in the matrix element 22 from the container 12 by reason of capillary action. This result of movement of the perfume oil to the disk's upper surface occurs because as water saturates disk 26 the oil and water present will not mix and the oil is lighter than the water. This action continues until the water in container 12 is used up. The oil which rises to the upper surface of the disk 26 evaporates into the ambient and provides the deodorizing effects.

Even though there is the gap 28 already described between the bottom of the disk 26 and the top of the wick 22, it still turns out to be important to keep the water in the container 12 away from both of the matrix elements 22 and 26 until the room deodorizer 10 is ready for use. If this is not done there may be a tendency for the water to move up the wick 22 such that reverse capillary action will take place, and the perfume oil contained in disk matrix 26 will move, due to gravity, down the wick into the lower part of container 12. The oil will then become trapped in the bottom portion of container 12.

Accordingly, another feature of the invention resides in the arrangement for accomplishing this separation. In assembly of the deodorizer 10, approximately approximately three fluid ounces of water are placed into container 12 and the cylindrical matrix element or wick 22, having a width of approximately ½ inch, is placed into the bore 31 of the tube 18 (FIG. 1). The disk 26 is then placed inthe member 24 as already described, and the aforementioned 3 grams of perfume oil are added to disk 26. Then grill 32, having suitably spaced openings 32A is placed within the recess 25 in member 24, but is not pushed down. Only when the consumer desires to activate the device, as already described, is this open grill 32 pushed down such that the bottom 27 of disk 26 contacts the top 23 of wick 22.

As a consequence of the cover assembly 16 being snapped into position at the top edge or rim of container 12, a partial vacuum is created inside tube 18, whereby the water 14 will be precluded from entering opening 20 to start the capillary action.

As noted previously, the transparent outer cover 17 is provided for shipping and stacking purposes. To these ends, a recess or well 17A is formed at the top of outer cover 17; and a corresponding annular member 12A on container 12 is dimensioned to fit tightly into recess 17A.

Referring now to FIGS. 4–6 of the drawings, there will be seen an alternate embodiment to the previously described embodiment of FIGS. 1–3. In this latter embodiment there is seen a similar room deodorizing device 10' comprising a container 12' for holding the liquid 14'.

However, in place of the previous cover assembly 16 which featured a dome-like cover, the alternate embodiment has a flat top, cylindrical cover assembly 16', which is preferably formed integrally to include tube 18'; furthermore, the assembly 16' is provided with a cover member 24' whose base portion 24B' is adapted to be affixed to the top edge or rim of the container 12'. In addition, a raised portion 24A', of the cover member, which is of smaller diameter than the base portion 24B', accommodates the second matrix element 26' which makes contact with the first matrix element 22' retained in the bore 31' of tube 18'.

This second matrix element 26', in the shape of a disk, fits within a recess 28' in the raised portion 24A'; however, unlike the first preferred embodiment, is held down at all times for firm contact with the first matrix element 22' by means of an open grill member 32'. This open grill member is adapted to snap into raised portion 24A', thereby to hold the disk matrix 26' firmly against the top of the elongated cylindrical matrix element 22'.

This alternate embodiment is also provided with the partial vacuum feature already described in connection with the first preferred embodiment. Thus, a cap 34' is locked in place in an air-sealing relationship with raised portion 24A'; and the base portion 24B', which is provided with suitable depending peripheral portions 38' and 40', is pressed in position on the top edge or rim of container 12', thereby providing an air-tight, snap fit relationship with the container 12', and thereby insuring the partial vacuum. As before, the partial vacuum precludes water from entering opening 20' to start the capillary action.

While there have been shown and described what are considered at present to be the preferred embodiments of the present invention, it will be appreciated by those skilled in the art that modifications of such embodiments may be made. It is therefore desired that the invention not be limited to these embodiments, and it is intended to cover in the appended claims all such modifications as fall within the true spirit and scope of the invention.

I claim:

1. A room deodorizer adapted to continuously dispense a deodorant into a room over an extended time period of the order of 60 days comprising:

a container for holding a quantity of a first liquid that is not miscible with a second liquid;

a first matrix element partly immersed in said first liquid, and a second matrix element impregnated with said second liquid, said second matrix element being disposed above said first matrix element and communicating therewith such that the first liquid moves upward in the first matrix element by capillary action and contacts said second liquid impregnated in said second matrix element whereby the second liquid is forced to the surface by molecular displacement and evaporates into the atmosphere;

further including a cover assembly fitted to the top of said container, said cover assembly including a tube for accommodating said first matrix element and a hollow sleeve formed adjacent said tube;

said cover assembly including a cover member having a recess therein for receiving said second matrix element; a cap fitting over said cover member, said cap being provided with a rod adapted to extend into said hollow sleeve formed adjacent said tube, thereby to block an opening formed at the bottom of said sleeve such that water cannot reach said first matrix element.

2. A room deodorizer as defined in claim 1, in which said first and second matrix elements are composed of paper.

3. A room deodorizer as defined in claim 1, in which said cover assembly includes a cover member having a base portion and a raised portion of lesser diameter than the base portion for accommodating the second matrix element.

4. A room deodorizer as defined in claim 3, further including an open grill which fits over said second matrix element and is received within said cover member.

5. A room deodorizer as defined in claim 4, in which said open grill is adapted to be pushed down into a lower position from a higher position in said cover member so as to bring said second matrix element into contact with said first matrix element.

6. A room deodorizer adapted to continuously dispense a deodorant into a room over an extended time period of the order of 60 days comprising:

a container for holding a quantity of a first liquid that is not miscible with a second liquid;

a matrix having a first matrix element partly immersed in said first liquid, and having a second matrix element impregnated with said second liquid, said second matrix element being disposed above said first matrix element and communicating therewith such that the first liquid moves upward in the first matrix element by capillary action and contacts said second liquid impregnated in said second matrix element, whereby the second liquid is forced to the surface by molecular displacement and evaporates into the atmosphere;

further including a cover assembly fitted to the top of said container, said cover assembly including a tube for accommodating said first matrix element, and further including a cover member having a curved upper surface, and a recess in said cover member for receiving said second matrix element; and in which means are provided at the bottom of said recess for ensuring that a gap exists between the top of said first matrix element and the bottom of said second matrix element.

7. A room deodorizer as defined in claim 6, in which an open grill is disposed within said recess over said second matrix element; and further including a cap adapted to fit over said recess and to be received in a groove spaced circumferentially from said recess.

8. A room deodorizer as defined in claim 7, further including a tab on said cap, said tab being fashioned to conform closely with the curved upper surface of said cover member.

9. A device as defined in claim 8, in which means are provided on said cap such that the user is compelled to press down at the center of said cap for releasing said tab so that the tab can be manipulated to remove the cap from its groove, whereby said grill is coincidentally pushed down in contact with said second matrix element.

* * * * *